United States Patent [19]

Coffindaffer et al.

[11] Patent Number: 5,648,323

[45] Date of Patent: Jul. 15, 1997

[54] HIGH LATHER CONDITIONING SHAMPOOS WITH IMPROVED DEPOSITION OF INSOLUBLE, DISPERSED PHASE, FLUID CONDITIONING AGENT

[75] Inventors: Timothy Woodrow Coffindaffer; Philip Earl Cothran, both of Loveland, Ohio

[73] Assignee: The Procter & Gamble Company, Cincinnati, Ohio

[21] Appl. No.: 604,204

[22] Filed: Feb. 21, 1996

Related U.S. Application Data

[63] Continuation of Ser. No. 484,042, Jun. 7, 1995, abandoned, which is a continuation of Ser. No. 89,960, Jul. 12, 1993, abandoned.

[51] Int. Cl.$^6$ ................................ C11D 1/10; C11D 1/04
[52] U.S. Cl. .................... 510/122; 510/490; 510/488; 510/499; 510/126
[58] Field of Search ........................ 252/89.1, 173, 252/174.15, 546, 547, DIG. 13, DIG. 15; 510/122, 126, 488, 490, 499

[56] References Cited

U.S. PATENT DOCUMENTS

| | | | |
|---|---|---|---|
| 4,343,726 | 8/1982 | Egan et al. | 252/547 |
| 4,435,300 | 3/1984 | Guth et al. | 252/117 |
| 4,578,216 | 3/1986 | Fujii et al. | 252/542 |
| 4,741,855 | 5/1988 | Grote et al. | 252/142 |
| 4,772,424 | 9/1988 | Greeb | 252/546 |
| 4,832,872 | 5/1989 | Scandel | 252/547 |
| 4,837,013 | 6/1989 | Login et al. | 424/70 |
| 4,933,176 | 6/1990 | van Reeth | 424/70 |
| 4,954,335 | 9/1990 | Janchipraponvej | 424/70 |
| 4,976,953 | 12/1990 | Orr et al. | 424/47 |
| 5,085,857 | 2/1992 | Reid et al. | 424/70 |

FOREIGN PATENT DOCUMENTS

| | | | |
|---|---|---|---|
| 0400976 | 12/1990 | European Pat. Off. | A61K 7/075 |
| 0453238 | 10/1991 | European Pat. Off. | A61K 7/075 |

*Primary Examiner*—Ponnathapura Achutamurthy
*Attorney, Agent, or Firm*—Leonard W. Lewis; Anthony D. Sabatelli; David K. Dabbiere

[57] ABSTRACT

Provided are high lathering, conditioning shampoo compositions with improved deposition of nonvolatile, insoluble, dispersed phase fluid conditioning agent, said compositions comprising: (a) from about 5% to about 29.5%, by weight, of anionic surfactant selected from the group consisting of alkyl sulfates and alkyl ethoxylated sulfates, acids thereof, and mixtures thereof; (b) from about 0.5% to about 5%, by weight, of N-acylamino acid anionic surfactant and salts thereof; (c) from about 0.05% to about 10%, by weight, of nonvolatile, insoluble fluid conditioning agent dispersed in said composition; (d) from about 0.5% to about 10%, by weight, of crystalline suspending agent for said dispersed conditioning agent; (e) from about 40% to about 89%, by weight, of water; wherein the total detersive surfactant concentration in said composition is from about 10% to about 30%; the weight ratio of component (b):component (a) is at least about 1:20; and said composition is substantially free of betaine surfactants and alkanol amide foam boosters.

20 Claims, No Drawings

HIGH LATHER CONDITIONING SHAMPOOS WITH IMPROVED DEPOSITION OF INSOLUBLE, DISPERSED PHASE, FLUID CONDITIONING AGENT

This is a continuation of application Ser. No. 08/484,042, filed on Jun. 7, 1995, abandoned, which is a continuation of application Ser. No. 08/089,960, filed Jul. 12, 1993 abandoned.

TECHNICAL FIELD

The present invention relates to shampoo compositions containing insoluble, dispersed phase, fluid conditioning agents. In particular, the present invention relates to shampoo compositions containing insoluble, dispersed phase, fluid conditioning agents suspended by a crystalline suspending agent.

BACKGROUND OF THE INVENTION

Shampoo compositions for cleaning hair which also contain conditioning agents are well known. Among the preferred types of conditioning agents are nonvolatile, insoluble, fluid conditioning agents such as polydimethylsiloxane and other silicone polymers. Silicone conditioners are particularly valued for their ability to provide a smooth, soft feel to dry hair. Other common insoluble fluid conditioners include organic fluids, e.g. oils, such as hydrocarbons and fatty esters. These conditioners are valued for their ability to replace natural oils lost from the hair due to cleansing surfactants in shampoos, and to add sheen and luster to the hair. In order for these types of shampoos to be effective and to provide a consistent level of performance, without necessitating vigorous shaking of the package in which they are contained, it is necessary to suspend them in the composition with the aid of a suspending agent. Furthermore, since shampoos are likely to remain on shelves or in storage for long periods of time, it is important for the suspending agents to keep the conditioning agents well suspended for long periods of time. The suspending agents which are preferred for suspension of insoluble, dispersed phase fluid conditioning agents are those which form a crystalline network in the shampoo when not exposed to shear, such as when the shampoo is being stored on the shelf, but which allow the composition to be readily flowable when shear is applied, such as when a user tilts a bottle of the shampoo in preparation to dispense a portion of it onto ones hand or hair. Examples of such suspending agents include ethylene glycol distearate and N, N-di-(hydrogenated tallow) amido benzoic acid.

Just as important as suspending the insoluble, dispersed phase fluid conditioning agents, the suspending agent must also allow the conditioning agent to deposit on the hair or scalp during use. If the conditioning agent does not deposit well, large proportions will likely be rinsed away and, therefore, the shampoo will be unable to provide good conditioning efficacy. Alternately, in order to provide good conditioning, relatively high levels of the conditioning agents would need to be incorporated into the shampoo composition. This would add additional cost to the product, reduce lathering, and present additional product stability concerns.

Obtaining good deposition of the conditioning agent is further complicated by the action of detersive, i.e. "cleaning", surfactants in the shampoo. Detersive surfactants are designed to carry away, or remove, oil, grease, dirt, and particulate matter in general from the hair and scalp. In addition, the detersive surfactants will interfere with deposition of the dispersed phase fluid conditioning agent, and carry away both non deposited and some deposited conditioning agent during rinsing. This effect makes effective deposition of the conditioning agent even more critical for providing efficacious, cost effective conditioning from a shampoo matrix.

Another important parameter in the formulation of conditioning shampoos is lathering. The consuming public often associates high lathering with effective cleaning, and prefers high lathering shampoos from an aesthetic standpoint. Unfortunately, crystalline suspending agents, which are highly effective at suspending insoluble dispersed phase fluid conditioning agents, also tend to adversely affect lathering performance. In addition, these types of conditioning actives themselves also reduce the ability of the shampoo to provide good lather. It has become conventional practice to enhance the lathering performance of these shampoos by increasing the level of, or adding, ingredients that promote high lathering. Common ingredients for this purpose include increased levels of alkyl sulfate surfactants, the addition or increase in the level of betaine amphoteric surfactants, and the addition of fatty ester (e.g. $C_{10}$–$C_{22}$) mono- and di- ($C_1$–$C_3$) alkanol amide foam boosters.

It has been found, however, that these ingredients which enhance lathering performance also decrease deposition of insoluble dispersed phase fluid conditioning agents from the shampoo matrix.

It is an object of this invention to provide high lathering conditioning shampoos containing suspended, insoluble, dispersed phase fluid conditioning agents which provide improved deposition of insoluble dispersed phase fluid conditioning agents.

This and other benefits of the present invention as may be or become apparent to one skilled in the art can be obtained according to the present invention, as described in the description which follows.

Unless otherwise indicated, all percentages are calculated by weight of the total composition, and all ratios are calculated on a weight basis. Unless otherwise indicated, ingredients are based on the active level and, therefore do not include carriers or by-products that may be included in commercially available materials.

SUMMARY OF THE INVENTION

The present invention provides high lathering, shampoo compositions with improved deposition of nonvolatile, insoluble fluid conditioning agent, said compositions comprising:

(a) from about 5% to about 29.5%, by weight, of anionic surfactant selected from the group consisting of alkyl sulfates and alkyl ethoxylated sulfates, acids thereof, and mixtures thereof;

(b) from about 0.5% to about 5%, by weight, of N-acylamino acid anionic surfactant and salts thereof;

(c) from about 0.05% to about 10%, by weight, of nonvolatile, insoluble fluid conditioning agent dispersed in said composition;

(d) from about 0.5% to about 10%, by weight, of crystalline suspending agent for said dispersed conditioning agent;

(e) from about 40% to about 89%, by weight, of water; wherein the total detersive surfactant concentration in said composition is from about 10% to about 30%; the weight ratio of component (b):component (a) is at least about 1:20;

and said composition is substantially free of betaine surfactants and alkanol amide foam boosters.

Unexpectedly enhanced deposition of the insoluble, dispersed conditioning agent can be obtained for the compositions of the present invention with retention of high quality lather, with the substitution of N-acylamino acid surfactant for betaines and alkanol amide foam boosters.

DETAILED DESCRIPTION OF THE INVENTION

Detersive Surfactant Component

The compositions of the present invention contain a detersive surfactant component, which necessarily comprises two types of anionic surfactants: (a) alkyl sulfate, alkyl ethoxylated sulfate, or a mixture thereof; and (b) N-acylamino acid surfactant. The compositions hereof can additionally comprise one or more other anionic surfactants, as well as nonionic, and amphoteric surfactants. The purpose of the detersive surfactant is to provide cleaning performance to the composition. The present compositions are, however, substantially free of betaine surfactant and alkanol amide foam boosters.

The total detersive surfactant component will generally be present at a level from about 10% to about 30%, by weight of the composition, preferably from about 12% to about 25%, more preferably from about 15% to about 22%.

Sulfate Surfactants

The compositions hereof will comprise alkyl sulfate, alkyl ethoxylated sulfate, or a mixtue thereof, as an essential surfactant component. Typically, such sulfate surfactants will collectively be present at a level of from about 5% to about 29.5%, preferably from about 10% to about 25%, more preferably from about 12% to about 22%, most preferably from about 15% to about 22%, by weight of the composition. These materials have the respective formulae (I) $ROSO_3M$ and (II) $RO(C_2H_4O)_xSO_3M$, wherein R is alkyl or alkenyl of from about 8 to about 30 carbon atoms, x is 1 to 10, and M is H or a soluble salt-forming cation such as ammonium, alkanolamine, such triethanolamine, monovalent metals, such as sodium and potassium, and polyvalent metal cations, such as magnesium and calcium. The cation M, of the anionic surfactant should be chosen such that the anionic surfactant component is water soluble. Solubility will depend upon the particular anionic surfactants and cations chosen. As an aid to determining appropriate mixtures of anionic surfactants, the anionic surfactants should be chosen such that the Krafft temperature of the surfactants chosen is about 15° C. or less, preferably about 10° C. or less, more preferably about 0° C. or less. It is also preferred that the anionic surfactant be soluble in the composition hereof.

Preferably, R has from about 10 to about 18 carbon atoms in both the alkyl and alkyl ethoxylated sulfates. The alkyl ethoxylated sulfates are typically made as condensation products of ethylene oxide and monohydric alcohols having from about 8 to about 24 carbon atoms. The alcohols can be derived from fats, e.g., coconut oil, palm kernal oil, or tallow, or can be synthetic. Such alcohols are preferably reacted with about 1 to about 10, more preferably from about 1 to about 4, most preferably from about 2 to about 3.5, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 4 moles of ethylene oxide.

N-Acylamino Acid Surfactant

The shampoo compositions of the present invention comprise from about 0.5% to about 5%, preferably from about 0.7% to about 4%, more preferably from about 1% to about 3%, of N-acyl amino acid surfactant.

N-acyl amino acid surfactants, for purposes hereof, include N-acyl hydrocarbyl acids and salts thereof, such as those represented by Formula III, as follows:

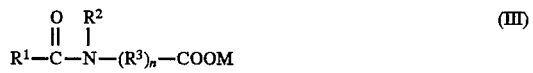

wherein: $R^1$ is a $C_8$–$C_{24}$ alkyl or alkenyl radical, preferably $C_{10}$–$C_{18}$; $R^2$ is —H, $C_1$–$C_4$ alkyl, phenyl, or —$CH_2COOM$, preferably $C_1$–$C_4$ alkyl, more preferably $C_1$–$C_2$ alkyl; $R^3$ is —$CR^4_2$— or $C_1$–$C_2$ alkoxy, wherein each $R^4$ independently is —H or $C_1$–$C_6$ alkyl or alkylester, and n is from 1 to 4, preferably 1 or 2; and M is —H or a cation as previously defined, preferably an alkali metal such as sodium or potassium.

A wide variety of N-acyl acid surfactants and their synthesis are described in *Anionic Surfactants*, Part II, *Surfactant Science Series*, Vol. VII, edited by Warner M. Linfield, Marcel Dekker, Inc. (New York and Basel), 1976; pp 581–617.

Especially preferred are compounds of Formula III wherein $R^2$ is methyl and $R^3$ is —$CH_2$—, and n is 1, which are known as the N-acyl sarcosinates, and acids thereof. Specific examples include lauroyl sarcosinate, myristoyl sarcosinate, cocoyl sarcosinate, and oleoyl sarcosinate, preferably in their sodium and potassium salt forms. Suitable N-acyl sarcosinates including the $C_{12}$–$C_{22}$ alkyl sarcosinates and acids thereof.

For the purposes of the surfactants described herein, it should be understood that the terms "alkyl" or "alkenyl" include mixtures of radicals which may contain one or more intermediate linkages such as ether or polyether linkages or non-functional substituents such as hydroxyl or halogen radicals wherein the radical remains of hydrophobic character.

Ratio of N-Acylamino Acid Surfactant:Sulfate Surfactant

The weight ratio of the N-acylamino acid surfactant:sulfate surfactant (total of the alkyl sulfate and alkyl ethoxylated sulfate) should be at least about 1:20, preferably from about 1:18 to about 1:1, more preferably from about 1:12 to about 1:4. The level of N-acylamino acid surfactant used should be sufficient to enhance foam and lather of the shampoo while also enhancing deposition of the insoluble, dispersed conditioning agent. The upper limit on the above ratio is practical in nature, due to the relatively high cost of the N-acylamino acid surfactant, and reduced cleaning performance when lower amounts of the sulfate surfactants are used.

Ratio of Alkyl Sulfate:Alkyl Ethoxylated Sulfate

The sulfate surfactant of the present invention can be comprised entirely of alkyl sulfate or alkyl ethoxylated sulfated, but preferably is a combination of these ethoxylated and nonethoxylated species. The weight ratio of alkyl sulfate to alkyl ethoxylated sulfate is preferably from about 4:1 to about 1:10, more preferably from about 2:1 to about 1:8, even more preferably from about 1:1 to about 1:5, most preferably from about 1:2 to about 1:4. Weight ratios as described above are preferred for their ability to provide optimum combinations of lather, cleaning, and conditioning agent performance. Alkyl sulfates can provide excellent cleaning and lather performance. Alkyl ethoxylated sulfates can provide excellent cleaning performance, are mild to the skin, and can enhance deposition of the insoluble, dispersed fluid conditioning agent relative to alkyl sulfates.

Substantially Free of Betaine Surfactants and Amide Foam Booster

The present compositions are substantially free of betaine surfactants and amide foam boosters. By "substantially free", what is meant is that the composition hereof can contain no more than about 1%, by weight, of each of these materials, preferably no more than about 0.5%, more preferably no more than about 0.25%, most preferably essentially zero percent. The presence of betaine surfactants and amide foam boosters can adversely affect deposition of the insoluble, dispersed fluid conditioning agent of the present invention.

Betaine surfactants to be excluded include those represented by the Formula (IV):

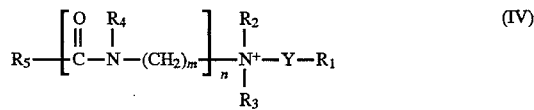

wherein:

$R_1$ is a member selected from the group consisting of

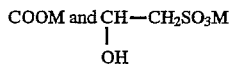

$R_2$ is $C_1$–$C_3$ alkyl or hydroxy ($C_1$–$C_3$) alkyl;

$R_3$ is $C_1$–$C_3$ alkyl or hydroxy ($C_1$–$C_3$) alkyl;

$R_4$ is a member selected from the group consisting of hydrogen and $C_1$–$C_3$ alkyl;

$R_5$ is $C_8$–$C_{20}$ alkyl or alkenyl;

Y is $C_1$–$C_3$ alkyl;

m is an integer from 2 to 7;

n is the integer 1 or 0;

M is hydrogen or a cation, such as an alkali metal or alkaline earth cation metal, ammonium, or alkanolamide.

The term "alkyl" or "hydroxyalkyl" means straight or branch chained, saturated, aliphatic hydrocarbon radicals and substituted hydrocarbon radicals such as, for example, methyl, ethyl, propyl, isopropyl, hydroxypropyl, hydroxyethyl, and the like.

The present shampoo compositions are also substantially free of amide foam boosters, such as fatty ester (e.g., $C_{10}$–$C_{22}$) mono- and di-($C_1$–$C_5$, especially $C_1$–$C_3$) alkanol amides.

The compositions of the present invention are also preferably substantially free of other ingredients which unduly decrease deposition, especially ingredients which do not provide a significant benefit to the composition.

Optional Surfactants

A suitable class of optional anionic detersive surfactants are aliphatic sulfonates such as represented by the water-soluble salts of the organic, sulfuric acid reaction products of the general formula (V):

wherein $R_1$ is chosen from the group consisting of a straight or branched chain, saturated aliphatic hydrocarbon radical having from about 8 to about 24, preferably about 12 to about 18, carbon atoms; and M is a cation, as previously described, subject to the same limitations regarding polyvalent metal cations as previously discussed. Important examples are the salts of an organic sulfuric acid reaction product of a hydrocarbon of the methane series, including iso-, neo-, and n-paraffins, having about 8 to about 24 carbon atoms, preferably about 12 about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12}$–$C_{18}$ paraffins (e.g. normal and secondary paraffins).

Additional examples of synthetic anionic detersive surfactants which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other synthetic anionic detersive surfactants of this variety are set forth in U.S. Pat. Nos. 2,486,921; 2,486,922; and 2,396,278.

Still other synthetic anionic detersive surfactants are in the class designated as succinates. This class includes such surface active agents as disodium N-octadecylsulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; dioctyl esters of sodium sulfosuccinic acid.

Other suitable anionic detersive surfactants include olefin sulfonates having about 12 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example, by liquid $SO_2$, chlorinated hydrocarbons, etc., when used in the liquid form, or by air, nitrogen, gaseous $SO_2$, etc., when used in the gaseous form.

The alpha-olefins from which the olefin sulfonates are derived are mono-olefins having about 12 to about 24 carbon atoms, preferably about 14 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific alpha-olefin sulfonate mxiture of the above type is described more fully in the U.S. Pat. No. 3,332,880, Pflaumer and Kessler, issued Jul. 25, 1967, incorporated herein by reference.

Another class of anionic detersive surfactants are the beta-alkyloxy alkane sulfonates. These compounds have the following formula (VI):

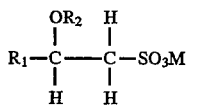

(VI)

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described.

Many additional synthetic anionic surfactants are described in *McCutcheon's Emulsifiers and Detergents*, 1989 Annual, published by M. C. Publishing Co., which is incorporated herein by reference. Also U.S. Pat. No. 3,929,678, Laughlin et al., issued Dec. 30, 1975, discloses many other anionic as well as other surfactant types and is incorporated herein by reference.

Preferred anionic detersive surfactants for use in the present shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric Surfactants

Examples of amphoteric surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate.

The amphoteric surfactant hereof include the imidazolinium amphoteric surfactants such as thoses depicted by Formula VII:

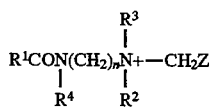

VII wherein $R^1$ is $C_8$–$C_{22}$ alkyl or alkenyl, preferably $C_{12}$–$C_{16}$, $R^2$ hydrogen or $CH_2CO_2M$, $R^3$ is $CH_2CH_2OH$ or $CH_2CH_2OCH_2CH\ COOM$, $R^4$ is hydrogen, $CH_2CH_2OH$, or $CH_2CH_2OCH_2CH_2COOM$, Z is $CO_2M$ or $CH_2CO_2M$, n is 2 or 3, preferably 2, M is hydrogen or a cation, such as alkali metal, alkaline earth metal, ammonium, or alkonol ammonium.

Suitable materials of this type are marketed under the tradename MIRANOL and are understood to comprise a complex mixture of species, and can exist in protonated and non-protonated species depending upon pH with respect to species that can have a hydrogen at $R^2$. The imidazolinum amphoteric surfactant hereof can be derived via an imidazolinium intermediate. However, it will be recognized by thosed in the art that it needn't necessarily be derived via an imidazolinium.

Preferred amphoteric surfactants of Formula VII are monocarboxylates and dicarboxylates. Examples of these materials include cocoamphocarboxypropionate, cocoamphocarboxypropionic acid, cocoamphocarboxyglycinate (alternately referred to as cocoamphodiacetate), and cocoamphoacetate.

Specific commercial products providing the imidazolinium derivative component of the present compositions include those sold under the trade names MIRANOL C2M CONC. N.P., MIRANOL C2M CONC. O.P., MIRANOL C2M SF, MIRANOL CM SPECIAL (Miranol, Inc.); ALK-ATERIC 2CIP (Alkaril Chemicals); AMPHOTERGE W-2 (Lonza, Inc.); MONATERIC CDX-38, MONATERIC CSH-32 (Mona Industries); REWOTERIC AM-2C (Rewo Chemical Group); and SCHEROTERIC MS-2 (Scher Chemicals).

Amphoteric surfactants also include aminoalkanoates of the formula (VIII):

(VIII)

and iminodialkanoates of the formula (IX):

(IX)

and mixtures thereof; wherein n and m are numbers from 1 to 4, R is $C_8$–$C_{22}$ alkyl or alkenyl, and M is hydrogen, alkali metal, alkaline earth metal, ammonium or alkanolammonium.

Examples of such amphoteric surfactants include n-alkylaminopropionates and n-alkyliminodipropionates. Such materials are sold under the tradename DERIPHAT by Henkel and MIRATAINE by Miranol, Inc. Specific examples include N-lauryl-beta-amino propionic acid or salts thereof, and N-lauryl-beta-imino-dipropionic acid or salts thereof.

Nonionic Surfactants

Nonionic detersive surfactants which can be used include those broadly defined as compounds produced by the condensation of alkylene oxide groups (hydrophilic in nature) with an organic hydrophobic compound, which may be aliphatic or alkyl aromatic in nature. Examples of preferred classes of nonionic detersive surfactants are:

1. The polyethylene oxide condensates of alkyl phenols, e.g., the condensation products of alkyl phenols having an alkyl group containing from about 6 to about 20 carbon atoms in either a straight chain or branched chain configuration, with ethylene exode, the said ethylene oxide being present in amounts equal to from about 10 to about 60 moles of ethylene oxide per mole of alkyl phenol.

2. Those derived from the condensation of ethylene oxide with the product resulting from the reaction of propylene oxide and ethylene diamine products.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. the arrow in the formula is a conventional representation of a semipolar bond.

5. Long chain tertiary phosphine oxides corresponding to the following general formula:

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety.

7. Alkyl polysaccharide (APS) surfactants such as the alkyl polyglycosides. Such surfactants are described in U.S. Pat. No. 4,565,647, Llenado, issued Jan. 21, 1986, incorporated herein by reference, which discloses APS surfactants having a hydrophobic group with about 6 to about 30 carbon atoms and polysaccharide (e.g., polyglycoside) as the hydrophilic group. Optionally, there can be a polyalkylene-oxide group joining the hydrophobic and hydrophilic moieties. The alkyl group (i.e., the hydrophobic moiety) can be saturated or unsaturated, branched or unbranched, and unsubstituted or substituted (e.g., with hydroxy or cyclic rings).

8. Polyethylene glycol (PEG) glyceryl fatty esters, such as those of the formula $R(O)OCH_2CH(OH)CH_2(OCH_2CH_2)_nOH$ wherein n is from about 5 to about 200, preferably from about 20 to about 100, and R is an aliphatic hydrocarbyl having from about 8 to about 20 carbon atoms.

When used, optional surfactants are typically present at levels of from about 0.05% to about 20%, more typically from about 0.1% to about 10%, preferably from about 0.5% to about 5%, although higher or lower levels can be used.

Insoluble, Emulsified, Fluid Hair Conditioning Agent

The present compositions will comprise from about 0.05% to about 10%, preferably from about 0.1% to about 8%, more preferably from about 0.2% to about 5%, by weight, of a dispersed phase, i.e., an emulsion, of a water insoluble, nonvolatile, fluid hair conditioning agent. This component will be suspended in the form of droplets, which form a separate, discontinuous phase from the aqueous, continuous phase of the compositions. Number average droplet size is not critical to the invention, but is typically up to about 30 microns, preferably up to about 25 microns, and will typically be at least about 0.1 microns, more typically at least about 2 microns. The particular amount used is not critical as long as an effective amount is present to provide a conditioning benefit and the conditioning agent is stably suspended by the suspending agent. In general, the least amount of the conditioning agent to achieve the desired level of conditioning is preferred, to optimize lathering performance, to reduce the amount of suspending agent required, and to minimize cost. Suitable fluid hair conditioning agents of this type include nonvolatile silicone hair conditioning agents and organic fluids, e.g. oils.

By "nonvolatile" what is meant is that the liquid exhibits very low or no significant vapor pressure at ambient conditions (e.g., 25° C.), as is understood in the art, in general, less than 0.2 mm Hg (preferably less than 0.1 mm) at 25° C. The nonvolatile oil preferably has a boiling point at ambient pressure of about 250° C. or higher, more preferably about 275° C. or higher, most preferably about 300° C. or higher. Mixtures of the conditioning agents can be used. Individual components of the conditioning agent which are miscible may fall outside the boiling point limits, as long as the overall conditioning agent is nonvolatile as defined above.

By "water insoluble" what is meant is that the material is not soluble in water (distilled or equivalent) at a concentration of 0.1%, at 25° C.

Silicone Hair Conditioning Agent

The nonvolatile, water insoluble silicone hair conditioning agent component of the present invention is nonvolatile and insoluble in the composition. It will be intermixed in the shampoo composition so as to be in the form of an emulsion, i.e., a separate, discontinuous phase of dispersed, insoluble droplets. These droplets are suspended with a suspending agent, numerous, nonexclusive suitable examples of which are described below. This dispersed silicone conditioning component will comprise a silicone fluid hair conditioning agent and can also comprise other ingredients, such as a silicone resin to enhance silicone fluid deposition efficiency or enhance glossiness of the hair (especially when high refractive index (e.g. above about 1.46) silicone conditioning agents are used (e.g. highly phenylated silicones).

The silicone hair conditioning agent phase may comprise volatile silicone components. Typically, if volatile silicones are present, it will be incidental to their use as a solvent or carrier for commercially available forms of nonvolatile silicone materials ingredients, such as silicone gums and resins.

The silicone hair conditioning agent component for use herein will preferably have viscosity of from about 20 to about 2,000,000 centistokes at 25° C., more preferably from about 1,000 to about 1,800,000, even more preferably from about 50,000 to about 1,500,000, most preferably from about 100,000 to about 1,500,000. The viscosity can be measured by means of a glass capillary viscometer as set forth in Dow Corning Corporate Test Method CTM0004, Jul. 20, 1970.

The silicone hair conditioning agent component will generally be used in the shampoo compositions hereof at levels of from about 0.05% to about 10% by weight of the composition, preferably from about 0.1% to about 8%, more preferably from about 0.2% to about 5%, most preferably from about 0.5% to about 4%. The minimum level that is used in a particular composition should be effective to provide a conditioning benefit. The maximum level that can be used is not limited by theory, but rather by practicality. It is generally unnessary and expensive to use levels in excess of about 8%, although higher levels can be used if desired.

One type of silicone fluid that can be used herein is a silicone oil. The term "silicone oil" shall mean flowable silicone materials having a viscosity of less than 1,000,000 centistokes at 25° C. Generally, the viscosity of the fluid will be between about 5 and 1,000,000 centistokes at 25° C., preferably between about 10 and about 100,000. Suitable silicone oils include polyalkyl siloxanes, polyaryl siloxanes, polyalkylaryl siloxanes, polyether siloxane copolymers, and mixtures thereof. Other insoluble, nonvolatile silicone fluids having hair conditioning properties can also be used.

More particularly silicone oils hereof include polyalkyl or polyaryl siloxanes with the following structure (XI):

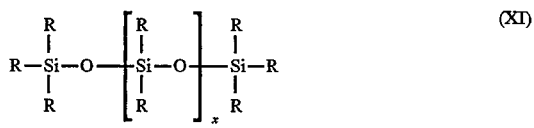

wherein R is aliphatic, preferably alkyl or alkenyl, or aryl, R can be substituted or unsubstituted, and x is an integer from 1 to about 8,000. Suitable unsubstituted R groups include alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, are insoluble in the composition, and are capable of being deposited on and, of conditioning, the hair.

The two R groups on the silicon atom of each monomeric silicone unit may represent the same group or different groups. Preferably, the two R groups represent the same group.

Preferred alkyl and alkenyl substituents are $C_1$–$C_5$ alkyls and alkenyls, more preferably from $C_1$–$C_4$, most preferably from $C_1$–$C_2$. The aliphatic portions of other alkyl-, alkenyl-, or alkynyl-containing groups (such as alkoxy, alkaryl, and alkamino) can be straight or branched chains and preferably have from one to five carbon atoms, more preferably from one to four carbon atoms, even more preferably from one to three carbon atoms, most preferably from one to two carbon atoms. As discussed above, the R substituents hereof can also contain amino functionalities, e.g. alkamino groups, which can be primary, secondary or tertiary amines or quaternary ammonium. These include mono-, di- and tri-alkylamino and alkoxyamino groups wherein the aliphatic portion chain length is preferably as described above. The R substituents can also be substituted with other groups, such as halogens (e.g. chloride, fluoride, and bromide), halogenated aliphatic or aryl groups, and hydroxy (e.g. hydroxy substituted aliphatic groups). Suitable halogenated R groups could include, for example, tri-halogenated (preferably fluoro) alkyl groups such as —$R^1$—C(F)$_3$, wherein $R^1$ is $C_1$–$C_3$ alkyl. Examples of such polysiloxanes include polymethyl-3,3,3 trifluoropropylsiloxane.

The nonvolatile polyalkylsiloxane fluids that may be used include, for example, polydimethylsiloxanes. These siloxanes are available, for example, from the General Electric Company in their Viscasil R and SF 96 series, and from Dow Corning in their Dow Corning 200 series.

Other suitable R groups include methyl, methoxy, ethoxy, propoxy, and aryloxy. The three R groups on the end caps of the silicone may also represent the same or different groups.

Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Alkylamino substituted silicones that can be used herein include those of the formula:

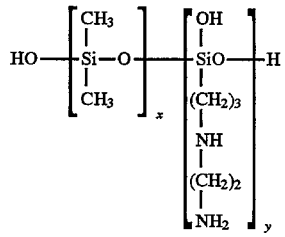

in which x and y are integers which depend on the molecular weight, the average molecular weight being approximately between 5,000 and 10,000. This polymer is also known as "amodimethicone".

Cationic silicone fluids which can be used in the present compositions include those that correspond to the formula:

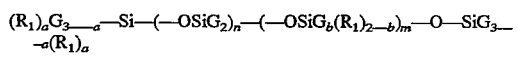

in which G is chosen from the group consisting of hydrogen, phenyl, OH, $C_1$–$C_8$ alkyl and preferably methyl; a denotes 0 or an integer from 1 to 3, and preferably equals 0;

b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10;

$R_1$ is a monovalent radical of formula $C_qH_{2q}L$ in which q is an integer from 2 to 8 and L is chosen from the groups

—N($R_2$)CH$_2$—CH$_2$—N($R_2$)$_2$

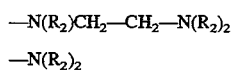

—N⁺(R₂)₃A⁻

—N⁺(R₂)CH₂—CH₂—N⁺R₂H₂A⁻ in which R₂ is chosen from the group consisting of hydrogen, phenyl, benzyl, a saturated hydrocarbon radical, preferably an alkyl radical containing from 1 to 20 carbon atoms, and A⁻ denotes a halide ion.

An especially preferred cationic silicone corresponding to formula immediately above is the polymer known as "trimethylsilylamodimethicone", of formula:

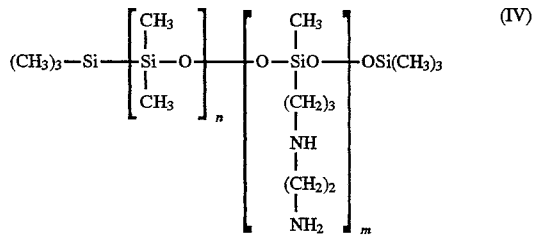

Other silicone cationic polymers which can be used in the present compositions correspond to the formula:

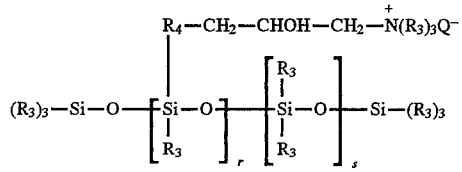

in which

R₃ denotes a monovalent hydrocarbon radical having from 1 to carbon atoms, and more especially an alkyl or alkenyl radical such as methyl;

R₄ denotes a hydrocarbon radical such as, preferably a $C_1$–$C_{18}$ alkylene radical or a $C_1$–$C_{18}$, and preferably $C_1$–$C_8$, alkyleneoxy radical;

Q' is a halide ion, preferably chloride;

r denotes an average statistical value from 2 to 20, preferably from 2 to 8;

s denotes an average statistical value from 20 to 200, and preferably from 20 to 50.

These compounds are described in greater detail in U.S. Pat. No. 4,185,017.

A polymer of this class which is especially preferred is that sold by UNION CARBIDE under the name "UCAR SILICONE ALE 56".

Another silicone fluid that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. All of these described references are incorporated herein by reference. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

Preferably the silicone hair conditioning agent comprises a mixture of a polydimethylsiloxane gum, having a viscosity greater than about 1,000,000 centistokes and polydimethylsiloxane oil having a viscosity of from about 10 centistokes to about 100,000 centistokes, wherein the ratio of gum to fluid is from about 30:70 to about 70:30, preferably from about 40:60 to about 60:40.

Another category of nonvolatile, insoluble silicone fluid conditioning agents are high refractive index silicones, having a refractive index of at least about 1.46, preferably at least about 1.48, more preferably at least about 1.52, most preferably at least about 1.55. Although not intended to necessarily be limiting, the refractive index of the polysiloxane fluid will generally be less than about 1.70, typically less than about 1.60. Polysiloxane "fluid" includes oils as well as gums.

The high refractive index polysiloxane fluid suitable for purposes hereof includes those represented by general Formula (XI) above, as well as cyclic polysiloxanes such as those represented by the formula below:

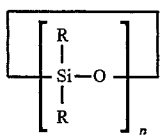

wherein R is as defined above, n is from about 3 to about 7, preferably from 3 to 5.

The high refractive index polysiloxane fluids hereof contain a sufficient amount of aryl-containing R substituents to increase the refractive index to the desired level, which is described above. In addition, R and n must be selected so that the material is nonvolatile, as defined above.

Aryl-containing substituents contain alicyclic and heterocyclic five and six membered aryl rings, and substituents containing fused five or six membered rings. The aryl rings themselves can be substituted or unsubstituted. Substituents include aliphatic substituents, and can also include alkoxy substituents, acyl substituents, ketones, halogens (e.g., Cl and Br), amines, etc. Exemplary aryl-containing groups include substituted and unsubstituted arenes, such as phenyl, and phenyl derivatives such as phenyls with $C_1$–$C_5$ alkyl or alkenyl substituents, e.g., allylphenyl, methyl phenyl and ethyl phenyl, vinyl phenyls such as styrenyl, and phenyl alkynes (e.g. phenyl $C_2$–$C_4$ alkynes). Heterocyclic aryl groups include substituents derived from furan, imidazole, pyrrole, pyridine, etc. Fused aryl ring substituents include, for example, napthalene, coumarin, and purine.

In general, the high refractive index polysiloxane fluids hereof will have a degree of aryl-containing substituents of at least about 15%, preferably at least about 20%, more preferably at least about 25%, even more preferably at least about 35%, most preferably at least about 50%. Typically, although it is not intended to necessarily limit the invention, the degree of aryl substitution will be less than about 90%, more generally less than about 85%, preferably from about 55% to about 80%.

These polysiloxane fluids are also characterized by relatively high surface tensions as a result of their aryl substitution. In general, the polysiloxane fluids hereof will have a surface tension of at least about 24 dynes/cm², typically at least about 27 dynes/cm². Surface tension, for purposes hereof, is measured by a de Nouy ring tensiometer according to Dow Corning Corporate Test Method CTM 461, Nov. 23, 1971. Changes in surface tension can be measured according to the above test method or according to ASTM Method D 1331.

The preferred high refractive index polysiloxane fluids hereof will have a combination of phenyl or phenyl derivative substituents (preferably phenyl), with alkyl substituents, preferably $C_1$–$C_4$ alkyl (most preferably methyl), hydroxy, $C_1$–$C_4$ alkylamino (especially —$R^1NHR^2NH2$ where each $R^1$ and $R^2$ independently is a $C_1$–$C_3$ alkyl, alkenyl, and/or alkoxy.

High refractive index polysiloxane are available commercially from Dow Corning Corporation (Midland, Mich., U.S.A.) Huls America (Piscataway, N.J., U.S.A.), and General Electric Silicones (Waterford, N.Y., U.S.A.).

It is preferred to utilize high refractive index silicones in solution with a spreading agent, such as a silicone resin or a surfactant, to reduce the surface tension by a sufficient amount to enhance spreading and thereby enhance glossiness (subsequent to drying) of hair treated with the composition. In general, a sufficient amount of the spreading agent to reduce the surface tension of the high refractive index polysiloxane fluid by at least about 5%, preferably at least about 10%, more preferably at least about 15%, even more preferably at least about 20%, most preferably at least about 25%. Reductions in surface tension of the polysiloxane fluid/spreading agent mixture can provide improved shine enhancement of the hair.

Also, the spreading agent will preferably reduce the surface tension by at least about 2 dynes/cm$^2$, preferably at least about 3 dynes/cm$^2$, even more preferably at least about 4 dynes/cm$^2$, most preferably at least about 5 dynes/cm$^2$.

The surface tension of the mixture of the polysiloxane fluid and the spreading agent, at the proportions present in the final product, is preferably 30 dynes/cm$^2$ or less, more preferably about 28 dynes/cm$^2$ or less most preferably about 25 dynes/cm$^2$ or less. Typically the surface tension will be in the range of from about 15 to about 30, more typically from about 18 to about 28, and most generally from about 20 to about 25 dynes/cm$^2$.

The weight ratio of the highly arylated polysiloxane fluid to the spreading agent will, in general, be between about 1000:1 and about 1:1, preferably between about 100:1 and about 2:1, more preferably between about 50:1 and about 2:1, most preferably from about 25:1 to about 2:1. When fluorinated surfactants are used, particularly high polysiloxane: spreading agent ratios may be effective due to the efficiency of these surfactants. Thus is contemplated that ratios significantly above 1000:1 may be used.

References disclosing suitable silicone fluids include U.S. Pat. No. 2,826,551, Geen; U.S. Pat. No. 3,964,500, Drakoff, issued Jun. 22, 1976; U.S. Pat. No. 4,364,837, Pader; and British Patent 849,433, Woolston. All of these patents are incorporated herein by reference. Also incorporated herein by reference is Silicon Compounds distributed by Petrarch Systems, Inc., 1984. This reference provides an extensive (though not exclusive) listing of suitable silicone fluids.

An optional ingredient that can be included in the silicone conditioning agent is silicone resin. Silicone resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, and resins, as well as manufacture of silicones, can be found in Encyclopedia of Polymer Science and Engineering, Volume 15, Second Edition, pp 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetrafunctional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MDT and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid, having refractive index below 1.46, to the silicone resin component, when used, is preferably from about 4:1 to about 400:1, preferably this ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a pad of the same phase in the compositions hereof as the silicone fluid, i.e. the conditioning active, the sum of the fluid and resin should be included in determining the level of conditioning agent in the composition.

Organic Hair Conditioning Agent

The organic fluid hair conditioning agents hereof generally will have a viscosity of about 3 million cS or less, preferably about 2 million cS or less, more preferably about 1.5 million cS or less (as measured by a Wells-Brookfield cone and plate viscometer at a rate of 15/s, or equivalent). For purposes hereof, "organic" shall not include silicone hair conditioning agents.

The organic hair conditioning materials hereof include fluids selected from the group consisting of hydrocarbon fluids and fatty esters. The fatty esters hereof are characterized by having at least 10 carbon atoms, and include esters with hydrocarbyl chains derived from fatty acids or alochols, e.g., mono-esters, polyhydric alcohol esters, and di- and tri-carboxylic acid esters. The hydrocarbyl radicals of the fatty esters hereof can also include or have covalently bonded thereto other compatible functionalities, such as amides and alkoxy moieties (e.g., ethoxy or ether linkages, etc.).

Hydrocarbon fluids include oils such as cyclic hydrocarbons, straight chain aliphatic hydrocarbons (saturated or unsaturated), and branched chain aliphatic hydrocarbons (saturated or unsaturated), and mistures thereof. Straight chain hydrocarbon oils will preferably contain from about 12 to about 19 carbon atoms, although it is not necessarily meant to limit the hydrocarbons to this range. Branched chain hydrocarbon oils can and typically may contain higher numbers of carbon atoms. Also encompassed herein are polymeric hydrocarbons of alkenyl monomers, such as $C_2-C_6$ alkenyl monomers. These polymers can be straight or branched chain polymers. The straight chain polymers will typically be relatively shod in length, having a total number of carbon atoms as described above for straight chain hydrocarbons in general. The branched chain polymers can have substantially higher chain length. The number average molecular weight of such materials can vary widely, but will typically be up to about 500, preferably from about 200 to about 400, more preferably from about 300 to about 350. Specific examples of suitable materials include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eiocosane, such as 2,2,4,4,6,6,8, 8-dimethyl-10-methylundecane and 2,2,4,4,6, 6-dimethyl-8-methylnonane, sold by Permethyl Corporation. Polymeric organic materials are also useful conditioning agents. A preferred organic polymer is polybutene, such as the copolymer of isobutylene and butene. A commercially available material of this type if L-14 polybutene from Amoco Chemical Co. (Chicago, Ill., U.S.A.). Other polymeric conditioners can include polyisoprene, polybutadiene, and other hydrocarbon polymers of $C_4$ to $C_{12}$ straight and branched chain, mono- and di-unsaturated aliphatic monomers, and derivatives thereof.

Monocarboxylic acid esters hereof include esters of alcohols and/or acids of the formula R'COOR wherein alkyl or alkenyl radicals and the sum of carbon atoms in R' and R is at least 10, preferably at least 20.

Fatty esters include, for example, alkyl and alkenyl esters of fatty acids having aliphatic chains with from about 10 to about 22 carbon atoms, and alkyl and alkenyl fatty alcohol carboxylic acid esters having an alkyl and/or alkenyl alcohol-derived aliphatic chain with about 10 to about 22 carbon atoms, and combinations thereof. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

The mono-carboxylic acid ester however need not necessarily contain at least one chain with at least 10 carbon atoms, so long as the total number of aliphatic chain carbon atoms is at least 10. Examples include diisopropyl adipate, diisohexyl adipate, and diisopropyl sebacate.

Di- and tri-alkyl and alkenyl esters of carboxylic acids can also be used. These include, for example, esters of $C_4-C_8$ dicarboxylic acids such as $C_1-C_{22}$ esters (preferably $C_1-C_6$) of succinic acid, glutaric acid, adipic acid, hexanoic acid, heptanoic acid, and octanoic acid. Specific example include isocetyl stearyol stearate, diisopropyl adipate, and tristearyl citrate.

Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters for use herein.

Glycerides include mono-, di-, and tri-glycerides. More specifically, included are the mono-, di-, and tri-estres of glycerol and long chain carboxylic acids, such as $C_1-C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include triolein and tristearin glyceryl dilaurate. Preferred glycerides are di-, and tri-glycerides. Especially preferred are triglycerides.

Suspending Agent

The present compositions include a crystalline suspending agent.

The conditioning agent of the present invention can be selected from the group consisting of silicone fluids, hydrocarbon fluids, fatty esters, and mixtures thereof. Other suspending agents useful for suspending the conditioning agent (or other materials) and for thickening the compositions can optionally be used.

The crystalline suspending agent will be used at an effective level for suspending the conditioning agent. The suspension should, in general, be stable for at least one month at ambient temperature. Longer term shelf stability such as at least three months, preferably six months, most preferably at least about twenty-four months, is preferred. In general, the compositions hereof will comprise from about 0.5% to about 10%, by weight, of a crystalline suspending agent or combination thereof. The crystalline suspending agent is preferably present in the shampoo compositions hereof at a level of about 0.5% to about 5%, more preferably about 1% to about 4%, most preferably about 1% to about 3%.

Preferred crystalline suspending agents are acyl derivatives and amine oxides, especially acyl derivatives, expecially those which can be solubilized in a premix solution and then be recrystallized upon cooling. These materials will comprise long chain (e.g., $C_8$-$C_{22}$ preferably $C_{14}$-$C_{22}$, more preferably $C_{16}$-$C_{22}$) aliphatic groups, i.e., long chain acyl derivative materials and long chain amine oxides, as well as mixtures of such materials. Included are ethylene glycol long chain esters, alkanol amides of long chain fatty acids, long chain esters of long chain fatty acids, glyceryl long chain esters, long chain esters of long chain alkanolamides, and long chain alkyl dimethyl amine oxides, and mixtures thereof.

Examples of crystalline suspending agents are described in U.S. Pat. No. 4,741,855, Grote and Russell, issued May 3, 1988, incorporated herein by reference. Suitable suspending agents for use herein include ethylene glycol esters of fatty acids preferably having from about 14 to about 22 carbon atoms, more preferably 16–22 carbon atoms. More preferred are the ethylene glycol stearates, both mono and distearate, but particularly the distearate containing less than about 7% of the mono stearate. Other suspending agents include alkanol amides of fatty acids, preferably having from about 16 to about 22 carbon atoms, more preferably about 16 to 18 carbon atoms. Preferred alkanol amides are stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate); glyceryl esters (e.g., glyceryl distearate) and long chain esters of long chain alkanol amides (e.g., stearamide diethanolamide distearate, stearamide monoethanolamide stearate). Ethylene glycol esters of long chain carboxylic acids, long chain amine oxides, and alkanol amides of long chain carboxylic acids, in addition to the preferred materials listed above, may be used as suspending agents.

Suspending agents also include long chain amine oxides such as alkyl ($C_{16}$-$C_{22}$) dimethyl amine oxides, e.g., stearyl dimethyl amine oxide. If the compositions contain an amine oxide or a long chain acyl derivative which is a surfactant, the suspending function could also be provided by such amine oxide or acyl derivative, provided at least a portion of them are present in crystalline form, and additional suspending agent may not be needed.

Other long chain acyl derivatives that can be used include N, N-dihydrocarbyl ($C_{12}$-$C_{22}$, preferably $C_{16}$-$C_{18}$) amido benzoic acid and soluble salts thereof (e.g., Na and K salts), particularly N,N-di($C_{16}$-$C_{18}$, and hydrogenated tallow) amido benzoic acid species of this family, which are commercially available from Stepan Company (Northfield, Ill., USA).

The crystalline suspending agent serves to assist in suspending the dispersed phase fluid conditioning agent, or other particulate matter or emulsions of insoluble fluids, in the shampoo compositions hereof, and may give pearlescence to the product.

The crystalline suspending agent can be selected from the group consisting of ethylene glycol long chain esters, and N,N-dihydrocarbyl amide benzoic acids and salts thereof, and mixtures thereof.

The crystalline suspending agent can be incorporated into the shampoos hereof by solubilizing it into a solution containing water and the anionic sulfate surfactant at a temperature above the melting point of the suspending agent. The suspending agent is then recrystallized, typically by cooling the solution to a temperature sufficient to induce crystallization.

Optional suspending agent thickeners, and viscosity modifiers, etc., when used are in general used at a level of from about 0.01% to about 10%, most commonly from about 0.02% to about 5.0% by weight of the total composition.

In general, the level of optional suspending agent and other viscosity modifiers should preferably be as low as possible to achieve the benefit for which the material is added.

Optional suspending agents that can be used include polymeric thickeners, such as carboxyvinyl polymers. Preferred carboxyvinyl polymers are copolymers of acrylic acid crosslinked with polyallylsucrose as described in U.S. Pat. No. 2,798,053, Brown, issued Jul. 2, 1957, incorporated herein by reference. These polymers are provided by B. F. Goodrich Company as, for example, Carbopol 934, 940, 941, and 956.

A carboxyvinyl polymer is an interpolymer of a monomeric mixture comprising a monomeric olefinically unsaturated carboxylic acid, and from about 0.01% to about 10% by weight of the total monomers of a polyether of a polyhydric alcohol, which polyhydric alcohol conatins at least four carbon atoms to which are attached at least three hydroxyl groups, the polyether containing more than one alkenyl group per molecule. Other monoolefinic monomeric materials may be present in the monomeric mixture if desired, even in predominant proportion. Carboxyvinyl polymers are substantially insoluble in liquid, volatile organic hydrocarbons and are dimensionally stable on exposure to air.

Preferred polyhydric alcohols used to produce carboxyvinyl polymers include polyols selected from the class consisting of oligosaccharides, reduced derivatives thereof in which the carbonyl group is converted to an alcohol group, and pentaerythritol; more preferred are oligosaccharides, most preferred is sucrose. It is preferred that the hydroxyl groups of the polyol which are modified be etherified with allyl groups, the polyol having at least two allyl ether groups per polyol molecule. When the polyol is sucrose, it is preferred that the sucrose have at least about five allyl ether groups per sucrose molecule. It is preferred that the polyether of the polyol comprise from about 0.01% to about 4% of the total monomers, more preferably from about 0.02% to about 2.5%.

Preferred monomeric olefinically unsaturated carboxylic acids for use in producing carboxyvinyl polymers used herein include monomeric, polymerizable, alpha-beta monoolefinically unsaturated lower aliphatic carboxylic acids; more preferred are monomeric monoolefinic acrylic acids of the structure (X):

where R is a substituent selected from the group consisting of hydrogen and lower alkyl groups; most preferred is acrylic acid.

Preferred carboxyvinyl polymers used in formulations of the present invention have a molecular weight of at least about 750,000; more preferred are carboxyvinyl polymers having a molecular weight of at least about 1,250,000; most preferred are carboxyvinyl polymers having a molecular weight of at least about 3,000,000.

Other materials can also be used as optional suspension agents include those that can impart a gel-like viscosity to the composition, such as water soluble or colloidally water soluble polymers like cellulose ethers (e.g., hydroxyethyl cellulose), guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

Another type of suspending agent that can be used is xanthan gum. Shampoo compositions utilizing xanthan gum as a suspending agent for the silicone hair conditioning component are described in U.S. Pat. No. 4,788,006, Bolich and Williams, issued Nov. 29, 1988, incorporated herein by reference. Xanthan gum is biosynthetic gum material that is commercially available. It is a heteropolysaccharide with a molecular weight of greater than 1 million. It is believed to contain D-glucose, D-mannose and D-glucuronate in the molar ratio of 2.8:2.0:2.0. The polysaccharide is partially acetylated with 4.7% acetyl. This information and other is found in Whistler, Roy L. Editor *Industrial Gums—Polysaccharides and Their Derivatives* New York: Academic Press, 1973. Kelco, a Division of Merck & Co., Inc. offers xanthan gum as Keltrol®. The gum, when used as the silicone hair conditioning component suspending agent, will typically be present in pourable, liquid formulations at a level of from about 0.02% to about 3%, preferably from about 0.03% to about 1.2%, in the compositions of the present invention.

Water

The compositions of the present invention will comprise from about 40% to about 89%, preferably from about 50% to about 85%, more preferably from about 60% to about 80%, by weight, of water.

The pH of the compositions hereof is not generally critical and may be in the range of from 2 to about 10, preferably from about 3 to about 9, more preferably from about 4 to about 8, most preferably from about 5.5 to about 7.5.

Optional Ingredients

A variety of other optional ingredients are described below. The description below is exemplary in nature.

Particulate Antidandruff Agent

The shampoo compositions optionally contain one or more particulate antidandruff agents as a preferred ingredient. A safe and effective amount of antidandruff active for control of dandruff on the scalp is used. Particulate antidandruff agents include, for example, sulfur, selenium sulfide, and pyridinethione salts. Preferred are heavy metal salts of 1-hydroxy-2-pyridinethione and selenium disulfide. The particulate antidandruff agents are in crystalline form and are insoluble in the compositions. In general, particulate antidandruff agents are used at levels of about 0.1% to about 5%, preferably from about 0.3% to about 5%, by weight of the composition. The particular amount used is not critical as long as an effective amount is used for controlling dandruff when the composition is used to shampoo the skin or hair in the conventional manner.

Selenium sulfide is a staple item of commerce. Selenium sulfide is generally regarded as a compound having one mole of selenium and two moles of sulfur. However, it may take the form of a cyclic structure, $Se_xS_y$, wherein x+y=8.

U.S. Pat. No. 2,694,668, Baldwin et al., issued Nov. 16, 1954; U.S. Pat. No. 3,152,046, Kapral, issued Oct. 6, 1984; U.S. Pat. No. 4,089,945, Brinkman, issued May 16, 1978; and U.S. Pat. No. 4,885,107, Wetzel, issued Dec. 12, 1989, all incorporated herein by reference, disclose selenium disulfide as an active ingredient in antidandruff shampoo compositions.

Selenium sulfide (selenium disulfide) preferably has an average of less than about 15µ, more preferably less than about 10µ. These measurements can be made using a forward laser light scattering device (e.g., a Malvern 3600 instrument).

If used, selenium sulfide is typically present in the shampoo compositions of this invention at a level of from about 0.1% to about 5.0%, preferably from about 0.3% to about 2.5%, more preferably from about 0.5% to about 1.5%, by weight of the composition.

Preferred pyridinethione antidandruff agents are water insoluble 1-hydroxy-2-pyridinethione salts. Preferred salts are formed from heavy metals such as zinc, tin, cadmium, magnesium, aluminium and zirconium. The most preferred metal herein is zinc. The most preferred active is the zinc salt of 1-hydroxy-2-pyridinethione, often referred to as zinc pyridinethione (ZPT). Other cations such as sodium may also be suitable. These types of antidandruff agents are well known in the art. 1-hydroxy-2-pyridinethione salts are disclosed for use in antidandruff shampoos in U.S. Pat. No. 2,809,971, Bernstein, issued Oct. 15, 1957; U.S. Pat. No. 3,236,733, Karsten et al., issued Feb. 22, 1966; U.S. Pat. No. 3,753,196 Parran, issued Aug. 21, 1973; U.S. Pat. No. 3,761,418, Parran, issued Sep. 25, 1973; U.S. Pat. No. 4,345,080, Bolich, issued Aug. 17, 1982; U.S. Pat. No. 4,323,683, Bolich et al., issued Apr. 6, 1982; U.S. Pat. No. 4,379,753, Bolich, issued Apr. 12, 1983; and U.S. Pat. No. 4,470,982, Winkler, issued Sep. 11, 1984; all incorporated herein by reference. Particularly preferred are those 1-hydroxy-2-pyridinethione salts in platelet particle form, wherein the particles have an average size of up to about 20 microns, preferably up to about 8 microns, most preferably up to about 5 microns.

The pyridinethione salts are generally used at a level of from about 0.1% to about 3%, preferably about 0.3% to about 2%, by weight of the shampoo composition.

Other particulate antidandruff actives include sulfur. Sulfur is typically used as an antidandruff agent at a level of from about 1% to about 5%, more preferably from about 2% to about 5%, by weight of the composition.

Additional optional ingredients include, for example, preservatives such as benzyl alcohol, methyl paraben, propyl paraben and imidazolidinyl urea; cationic conditioning agents, including both cationic conditioning surfactants and cationic conditioning polymers; quaternary polymeric foam boosters, such as Polyquaternium 10, preferably at a level of from about 0.01% to about 0.2%, by weight of the composition; fatty alcohols; block polymers of ethylene oxide and propylene oxide such as Pluronic F88 offered by BASF Wyandotte; sodium chloride, sodium sulfate; ammonium xylene sulfonate; propylene glycol; polyvinyl alcohol; ethyl alcohol; pH adjusting agents such as citric acid, succinic acid, phosphoric acid, sodium hydroxide, sodium carbonate, etc.; perfumes; and dyes. These optional ingredients are typically used at levels of from about 0.01% to about 10% of the composition. This list of optional ingredients is not meant to be exclusive, and other optional components can be utilized.

METHOD OF USE

The present compositions are used in a conventional manner for cleaning and conditioning hair. The compositions hereof can also be used and effective for cleaning and conditioning skin in a conventional manner. An effective amount of the composition, typically from about 1 g to about 20 g of the composition, for cleaning and conditioning the hair or skin is applied to hair, or other region of the body, that has preferably been wetted, generally with water, and then rinsed off. Application to the hair typically includes working the composition through the hair such that most or all of the hair is contacted with the composition.

EXAMPLES

The following Examples further describe and demonstrate the preferred embodiments within the scope of the present invention. The Examples are given solely for the purpose of illustration and are not to be construed as limitations of the present invention as many variations thereof are possible without departing from its spirit and scope.

Examples I-XV

The following examples exemplify shampoo compositions of the present invention.

The compositions are prepared as follows.

When applicable, a silicone premix is prepared by adding 70% Dimethicone, 29% Ammonium Laureth-3 Sulfate (solution basis, 26 wt. % active) and 1% Sodium Chloride, the percentages being on a weight basis of the silicone premix, to a high shear mixing vessel and mixing for about 30 minutes or until the desired silicone particle size is achieved (typically a number average particle size of from about 5 microns to about 25 microns).

For Examples I-XV, about one-third to all of the total alkyl sulfate surfactant (ammonium laureth-3 sulfate (added as a 26% solution) and/or ammonium lauryl sulfate (added as a 25% solution)) is added to a jacketed mix tank and heated to about 74° C. with slow agitation to form a surfactant solution. Sodium sulfate and fatty alcohol, as applicable, are added to the tank and allowed to disperse. Ethylene glycol distearate (EGDS) is then added to the mixing vessel, and melted. After the EGDS is well dispersed (usually about 5 to 20 minutes) polyethylene glycol and the preservative, if used are added and mixed into the surfactant solution. This mixture is passed through a heat exchanger where it is cooled to about 35° C. and collected in a finishing tank. As a result of this cooling step, the ethylene glycol distearate crystallizes to form a crystalline network in the product. The remainder of the ammonium laureth sulfate, lauryl sulfate and other ingredients including the silicone premix, if included in the formula, are added to the finishing tank with ample agitation to insure a homogeneous mixture. A sufficient amount of the silicone premix is added to provide the desired level of dimethicone in the final product. Polyquaternium 10, if added, is typically dispersed in water as a 0 1% solution before addition to the final mix. Once all ingredients have been added, ammonium xylene sulfonate or additional sodium sulfate can be added to the mixture to thin or thicken respectively to achieve a desired product viscosity. Preferred viscosities range from about 2500 to about 6000 cS at 25° C. (as measured by a Wells-Brookfield cone and plate viscometer at 15/s).

The compositions of the Examples can provide excellent in-use hair cleaning, lather, mildness, dandruff control (where applicable), and especially conditioning.

| Component (%, by weight, of composition) | I | II | III | IV | V |
|---|---|---|---|---|---|
| Sodium Laureth-3 Sulfate | 13.50 | 13.5 | 16.0 | 8.0 | 16.0 |
| Ammonium Lauryl Sulfate | 4.5 | 4.5 | 1.5 | 8.0 | 3.0 |
| Sodium Lauryl Sarcosinate 4 | 1.5 | 2.0 | 3.75 | 2.5 | 2.0 |
| Coconut ($C_{12}$-$C_{14}$) Fatty Alcohol | 0.17 | 0.34 | 0.0 | 0.0 | 0.0 |
| Polyquaternium 10 1 | 0.025 | 0.025 | 0.0 | 0.0 | 0.05 |
| Ethylene Glycol Distearate | 1.5 | 1.5 | 2.0 | 3.0 | 2.5 |
| Dimethicone 2 | 0.50 | 0.5 | 1.0 | 2.5 | 1.5 |
| Perfume Solution | 0.65 | 0.65 | 0.40 | 0.50 | 0.25 |
| DMDM Hydantoin | 0.20 | 0.20 | 0.30 | 0.30 | 0.30 |
| PEG 600 3 | 0.125 | 0.125 | 0.0 | 0.0 | 0.0 |
| Sodium Sulfate | 0.50 | 0.25 | 0.0 | 0.0 | 1.0 |
| Zinc Pyridinethione | 0.0 | 0 | 1.0 | 0.0 | 0.0 |
| Tricetylmethylammonium chloride | 0.0 | 0.15 | 0.55 | 0.0 | 0.0 |
| Color Solution (ppm) | 10 | 10 | 20 | 20 | 20 |
| Water and Minors | q. s. to 100% | | | | |

| Component (%, by weight, of composition) | VI | VII | VIII | IX | X |
|---|---|---|---|---|---|
| Sodium Laureth-3 Sulfate | 11.50 | 14.5 | 16.0 | 6.0 | 16.0 |
| Ammonium Lauryl Sulfate | 4.5 | 2.5 | 3.5 | 8.0 | 2.0 |
| Sodium Lauryl Sarcosinate 4 | 1.5 | 2.0 | 3.75 | 2.5 | 2.0 |
| Coconut ($C_{12}$-$C_{14}$) Fatty Alcohol | 0.1 | 0.0 | 0.0 | 0.1 | 0.0 |
| Polyquaternium 10 1 | 0.025 | 0.0 | 0.0 | 0.0 | 0.05 |
| Ethylene Glycol Distearate | 1.5 | 1.5 | 2.0 | 3.0 | 2.5 |
| Light Mineral Oil | 0.5 | 0.5 | 1.0 | 2.5 | 0.0 |
| Isopropyl Isostearate | 0.0 | 0.5 | 0.5 | 0.0 | 1.5 |
| Perfume Solution | 0.65 | 0.65 | 0.40 | 0.50 | 0.25 |
| DMDM Hydantoin | 0.20 | 0.20 | 0.30 | 0.30 | 0.30 |
| PEG 600 3 | 0.125 | 0.125 | 0.0 | 0.0 | 0.0 |
| Sodium Sulfate | 1.5 | 1.1 | 0.1 | 0.0 | 0.0 |
| Zinc Pyridinethione | 0.0 | 0 | 1.0 | 0.0 | 0.0 |
| Tricetylmethylammonium chloride | 0.0 | 0.15 | 0.55 | 0.0 | 0.0 |
| Color Solution (ppm) | 10 | 10 | 20 | 20 | 20 |
| Water and Minors | q. s. to 100% | | | | |

| Component (%, by weight, of composition) | XI | XII | XIII | XIV | VX |
|---|---|---|---|---|---|
| Sodium Laureth-3 Sulfate | 18.0 | 0.0 | 15.0 | 15.0 | 10.0 |
| Ammonium Lauryl Sulfate | 0.0 | 12.0 | 3.0 | 5.0 | 5.0 |
| Sodium Lauryl Sarcosinate 4 | 3.0 | 4.5 | 2.3 | 1.0 | 5.0 |
| Coconut ($C_{12}$-$C_{14}$) Fatty Alcohol | 0.0 | 0.0 | 0.0 | 0.0 | 0.0 |
| Polyquaternium 10 1 | 0.1 | 0.0 | 0.1 | 0.0 | 0.0 |
| Ethylene Glycol Distearate | 3.0 | 3.2 | 2.8 | 2.5 | 2.5 |
| Dimethicone 2 | 0.7 | 0.9 | 0.6 | 2.0 | 0.0 |
| Isocetyl Stearoyl Stearate | 0.0 | 0.0 | 1.0 | 0.5 | 2.0 |
| Perfume Solution | 0.9 | 0.35 | 0.30 | 0.7 | 1.1 |
| DMDM Hydantoin | 0.20 | 0.20 | 0.40 | 0.40 | 0.40 |
| PEG 600 3 | 0.0 | 0.3 | 0.0 | 0.0 | 0.20 |
| Sodium Sulfate | 0.0 | 0.0 | 0.0 | 0.0 | 0.0 |
| Zinc Pyridinethione | 2.0 | 1.0 | 0.0 | 0.0 | 1.0 |
| Tricetylmethylammonium chloride | 0.15 | 0.0 | 0.50 | 0.0 | 0.0 |
| Color Solution (ppm) | 10 | 10 | 20 | 20 | 25 |
| Water and Minors | q. s. to 100% | | | | |

1 UCARE Polymer JR-30M, commercially available from Union Carbide Corporation.
2 A 40(gum)/60(fluid) weight ratio blend of SE-76 dimethicone gum available from General Electric Silicones Division and a dimethicone fluid having a viscosity of 350 centistokes.
3 Polyethylene (600) glycol, a polymer of ethylene oxide having an average degree of polymerization of about 600.
4 Available under the tradename Hamposyl L-30 from Hampshire Chemical Corp. as a 30% active solution.

What is claimed is:

1. High lathering, conditioning shampoo compositions with improved deposition of dispersed phase, nonvolatile fluid conditioning agent, said compositions comprising:
   (a) from about 5% to about 29.5%, by weight, of anionic detersive surfactant selected from the group consisting of alkyl sulfates and alkyl ethoxylated sulfates, acids thereof, and mixtures thereof;
   (b) from about 0.5% to about 5%, by weight, of N-acylamino acid anionic detersive surfactant or salts thereof;
   (c) from about 0.05% to about 10%, by weight, of nonvolatile, water insoluble fluid conditioning agent dispersed in said composition;
   (d) from about 0.5% to about 10%, by weight, of crystalline suspending agent for said conditioning agent;
   (e) from about 40% to about 89%, by weight, of water;
wherein the total detersive surfactant concentration in said composition is from about 10% to about 30%; the weight ratio of component (b):component (a) is at least about 1:18; and said composition is substantially free of betaine surfactants and alkanol amide foam boosters.

2. A shampoo composition as in claim 1, wherein the weight ratio of component (b):component (a) is from about 1:18 to about 1:4.

3. A shampoo composition as in claim 1, wherein said composition comprises:
   (a) from about 10% to about 25%, by weight, of said alkyl sulfates and alkyl ethoxylated sulfates;
   (b) from about 0.7% to about 4%, by weight, of an N-acylamino acid surfactant, or salt thereof of the formula:

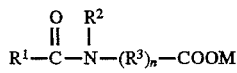

wherein: $R^1$ is a $C_8$–$C_{24}$ alkyl or alkenyl radical; $R^2$ is —H, $C_1$–$C_4$ alkyl, phenyl, or —CH$_2$COOM; $R^3$ is —CR$^4_2$— or $C_1$–$C_2$ alkoxy, wherein $R^4$ is —H or $C_1$–$C_6$ alkyl or alkylester; n is from 1 to 4; and M is —H or a cation;
   (c) from about 0.1% to about 8%, by weight, of nonvolatile, water insoluble fluid conditioning agent dispersed in said composition selected from the group consisting of silicone fluid and organic fluid conditioning agents;
   (d) from about 0.5% to about 5%, by weight, of a crystalline suspending agent for said conditioning agent;
   (e) from about 50% to about 85%, by weight, of water;
wherein: the total detersive surfactant concentration in said shampoo composition is from about 12% to about 25%; and the weight ratio of component b):component (a) is from about 1:18 to about 1:4.

4. A shampoo composition as in claim 3, wherein the weight ratio of component (b):component (a) is from about 1:12 to about 1:4.

5. A shampoo composition as in claim 3, wherein said conditioning agent is selected from the group consisting of silicone fluid and organic fluid conditioning agents, and mixtures thereof.

6. A shampoo composition as in claim 5, wherein said conditioning agent is selected from the group consisting of silicone fluids, hydrocarbon fluids, fatty esters, and mixtures thereof.

7. A shampoo composition as in claim 6, wherein said conditioning agent is a silicone fluid.

8. A shampoo composition as in claim 3, wherein said composition comprises from about 1% to about 4% of said suspending agent.

9. A shampoo composition as in claim 8, wherein said suspending agent is selected from the group consisting of ethylene glycol long chain esters, and N,N-dihydrocarbyl amido benzoic acids and salts thereof, and mixtures thereof.

10. A shampoo composition as in claim 1, wherein said component (b) surfactants are selected from the group consisting of $C_{12}$–$C_{22}$ alkyl sarcosinates, acids thereof, and mixtures thereof.

11. A shampoo composition as in claim 3, wherein said component (b) surfactants are selected from the group consisting of $C_{12}$–$C_{22}$ alkyl sarcosinates, acids thereof, and mixtures thereof.

12. A shampoo composition as in claim 1, further comprising a quaternary ammonium polymeric foam booster.

13. A shampoo composition, as in claim 12, comprising from about 0.01% to about 0.2%, by weight, of Polyquaternium 10.

14. A shampoo composition as in claim 3, wherein said composition comprises:
   (a) from about 12% to about 22%; by weight, of said alkyl sulfates and alkyl ethoxylated sulfates;
   b) from about 1% to about 3%, by weight, of an N-acylamino acid surfactant, or salt thereof of the formula:

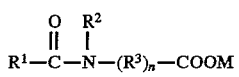

wherein: $R^1$ is a $C_{10}$–$C_{18}$ alkyl or alkenyl radical; $R^2$ is $C_1$–$C_4$ alkyl; $R^3$ is —CR$^4_2$— or $C_1$–$C_2$ alkoxy, wherein $R^4$ is —H or $C_1$–$C_6$ alkyl or alkylester; n is 1 or 2; and M is —H or a cation;
   (c) from about 0.2% to about 5%, by weight, of nonvolatile, water insoluble fluid conditioning agent dispersed in said composition selected from the group consisting of silicone fluid and organic fluid conditioning agents;
   (d) from about 1% to about 4%, by weight, of a crystalline suspending agent for said conditioning agent;
   (e) from about 50% to about 80%, by weight, of water;
wherein: the total detersive surfactant concentration in said shampoo composition is from about 15% to about 22%; and the weight ratio of component (b):component (a) is from about 1:12 to about 1:4.

15. A shampoo composition as in claim 14, wherein said suspending agent is selected from the group consisting of ethylene glycol long chain esters, and N,N-dihydrocarbyl amido benzoic acids and salts thereof, and mixtures thereof.

16. A shampoo composition as in claim 15, wherein said component (b) surfactants are selected from the group consisting of $C_{12}$–$C_{22}$ alkyl sarcosinates, acids thereof, and mixtures thereof.

17. A shampoo composition, as in claim 16, comprising from about 0.01% to about 0.2%, by weight, of Polyquaternium 10.

18. A composition according to claim 1 wherein the nonvolatile, water insoluble fluid conditioning agent is selected from the group consisting of hydrocarbon fluids, fatty esters and mixtures thereof.

19. A composition according to claim 7 further comprising silicone resin.

20. A high lathering, conditioning shampoo composition comprising:
- (a) from about 10% to about 25%, by weight, of anionic detersive surfactant selected from the group consisting of alkyl sulfates and alkyl ethoxylated sulfates, acids thereof, and mixtures thereof; said anionic detersive surfactant having a weight ratio of alkyl sulfate to alkyl ethoxylated sulfate of from about 1:2 to about 1:4;
- (b) from about 0.5% to about 5%, by weight, of N-acylamino acid anionic detersive surfactant selected from the group consisting of $C_{12}$–$C_{22}$ alkyl sarcosinates, acids thereof, and mixtures thereof;
- (c) from about 0.2% to about 5%, by weight, of nonvolatile, water insoluble silicone fluid conditioning agent;
- (d) from about 0.5% to about 5% by weight, of crystalline suspending agent selected from the group consisting of ethylene glycol long chain esters;
- (e) from about 60% to about 80%, by weight, of water; wherein the weight ratio of component (b):component (a) is at least about 1:20; and said composition is substantially free of betaine surfactants and alkanol amide foam boosters.

* * * * *